(12) United States Patent
Zhang et al.

(10) Patent No.: US 12,290,291 B2
(45) Date of Patent: May 6, 2025

(54) PROXIMAL-FEMUR INTRAOSSEOUS RELEASE DEVICE

(71) Applicant: The Fourth Medical Center of the Chinese People's Liberation Army General Hospital, Beijing (CN)

(72) Inventors: Licheng Zhang, Beijing (CN); Peifu Tang, Beijing (CN); Chi Ma, Beijing (CN); Xiang Cui, Beijing (CN); Pengbin Yin, Beijing (CN); Yong Xie, Beijing (CN); Junsong Wang, Beijing (CN)

(73) Assignee: The Fourth Medical Center of the Chinese People's Liberation Army General Hospital, Beijing (CN)

( * ) Notice: Subject to any disclaimer, the term of this patent is extended or adjusted under 35 U.S.C. 154(b) by 0 days.

(21) Appl. No.: 18/963,373

(22) Filed: Nov. 27, 2024

(65) Prior Publication Data
US 2025/0082377 A1   Mar. 13, 2025

(30) Foreign Application Priority Data
Dec. 12, 2023   (CN) .......................... 202311702387.0

(51) Int. Cl.
*A61B 17/74* (2006.01)
*A61B 17/02* (2006.01)
(Continued)

(52) U.S. Cl.
CPC .......... *A61B 17/74* (2013.01); *A61B 17/3472* (2013.01); *A61B 17/7258* (2013.01);
(Continued)

(58) Field of Classification Search
CPC ....... A61B 17/66; A61B 17/68; A61B 17/681; A61B 17/74; A61B 17/7094;
(Continued)

(56) References Cited

U.S. PATENT DOCUMENTS 4,590,930 A  *  5/1986  Kurth ................. A61B 17/7258
                                                         606/63
4,721,103 A  *  1/1988  Freedland .............. A61B 17/74
                                                         606/86 R
(Continued)

FOREIGN PATENT DOCUMENTS

CN    113974807 A    1/2022
CN    116746999 A    9/2023
(Continued)

*Primary Examiner* — Nathan R Price
*Assistant Examiner* — Mark A Igel

(57) ABSTRACT

A proximal-femur intraosseous release device includes a release mechanism. A primary fixing mechanism is provided at one end of the release mechanism, the primary fixing mechanism includes a first shell, and a second shell, a first triangular block and a second triangular block are arranged inside the first shell; the second shell is screwed to the first shell through threads, a bottom of the second shell is rotatably connected with the first triangular block, the first triangular block is slidably connected with the first shell, a bottom surface of the first triangular block is an inclined surface, the second triangular block is located at a bottom of the first triangular block, a top surface of the second triangular block is an inclined surface, and a through hole matched with the second triangular block is formed in the first shell.

10 Claims, 11 Drawing Sheets

(51) Int. Cl.
    *A61B 17/34*     (2006.01)
    *A61B 17/56*     (2006.01)
    *A61B 17/72*     (2006.01)
    *A61F 2/46*     (2006.01)
    *A61M 39/02*     (2006.01)

(52) U.S. Cl.
    CPC . *A61M 39/0247* (2013.01); *A61B 2017/0275* (2013.01); *A61B 2017/561* (2013.01); *A61F 2/4607* (2013.01); *A61M 2039/025* (2013.01)

(58) Field of Classification Search
    CPC .............. A61B 17/7098; A61B 17/742; A61B 17/3472; A61B 17/88; A61B 17/802; A61B 17/8805; A61B 17/8685; A61B 17/864; A61B 17/8095; A61B 17/8833; A61B 17/8819; A61B 17/8822; A61B 17/7258; A61B 2017/561; A61B 2017/0275; A61B 2017/603; A61M 2039/025; A61M 2210/02; A61M 2210/10; A61M 37/00; A61F 2/4607; A61F 2002/30677

See application file for complete search history.

(56) References Cited

U.S. PATENT DOCUMENTS

| | | | | |
|---|---|---|---|---|
| 5,415,660 | A * | 5/1995 | Campbell | A61B 17/7216 606/68 |
| 5,429,640 | A * | 7/1995 | Shuler | A61B 17/744 606/62 |
| 5,769,899 | A * | 6/1998 | Schwartz | A61F 2/30756 606/77 |
| 6,761,726 | B1 * | 7/2004 | Findlay | A61B 10/025 604/506 |
| 8,012,155 | B2 * | 9/2011 | Prygoski | A61B 17/7208 606/65 |
| 8,062,270 | B2 * | 11/2011 | Sweeney | A61B 17/8819 604/264 |
| 8,070,785 | B2 * | 12/2011 | Biscup | A61B 17/686 606/305 |
| 9,339,318 | B2 * | 5/2016 | Smith | A61B 17/88 |
| 10,172,654 | B2 * | 1/2019 | Watanabe | A61B 17/744 |
| 2001/0031254 | A1 * | 10/2001 | Bianchi | A61F 2/28 424/93.7 |
| 2002/0095214 | A1 * | 7/2002 | Hyde, Jr. | A61F 2/4612 623/908 |
| 2003/0083662 | A1 * | 5/2003 | Middleton | A61B 17/7098 606/92 |
| 2005/0015061 | A1 * | 1/2005 | Sweeney | A61B 17/7258 606/65 |
| 2006/0241776 | A1 * | 10/2006 | Brown | A61B 17/7225 623/22.32 |
| 2008/0269807 | A1 * | 10/2008 | Simon | A61B 17/746 606/301 |
| 2009/0181058 | A1 * | 7/2009 | Li | A61L 27/20 514/1.1 |
| 2010/0042214 | A1 * | 2/2010 | Nebosky | A61F 2/36 604/93.01 |
| 2011/0060373 | A1 * | 3/2011 | Russell | A61B 17/0401 606/86 R |
| 2011/0077651 | A1 * | 3/2011 | Lozier | A61B 17/7258 606/62 |
| 2011/0087227 | A1 * | 4/2011 | Mazur | A61B 17/7266 606/62 |
| 2011/0093020 | A1 * | 4/2011 | Wu | A61L 31/16 435/372 |
| 2011/0218582 | A1 * | 9/2011 | Smith | A61F 2/4609 606/86 R |
| 2012/0123423 | A1 * | 5/2012 | Fryman | A61B 17/175 606/89 |
| 2012/0203352 | A1 * | 8/2012 | Perez, III | A61F 2/3601 623/23.11 |
| 2013/0041414 | A1 * | 2/2013 | Epperly | A61B 17/7225 606/310 |
| 2014/0194811 | A1 * | 7/2014 | Barsoum | A61B 17/72 604/35 |
| 2014/0316531 | A1 * | 10/2014 | Klinger | A61F 2/3603 623/23.12 |
| 2016/0346025 | A1 * | 12/2016 | Bonutti | A61L 24/04 |
| 2016/0367371 | A1 * | 12/2016 | de Beaubien | A61F 2/38 |
| 2017/0035396 | A1 * | 2/2017 | Solomon | A61K 31/198 |
| 2017/0164986 | A1 * | 6/2017 | Chen | A61B 17/68 |
| 2018/0092674 | A1 * | 4/2018 | McDaniel | A61B 17/7291 |
| 2019/0083152 | A1 * | 3/2019 | Kuster | A61B 17/04 |
| 2021/0186578 | A1 * | 6/2021 | Chen | A61B 17/8858 |
| 2022/0110658 | A1 * | 4/2022 | Tierney | A61M 5/158 |
| 2023/0052651 | A1 * | 2/2023 | Sweeney | A61B 17/3472 |
| 2023/0248392 | A1 * | 8/2023 | Whittaker | A61B 17/7233 606/86 R |
| 2024/0016523 | A1 * | 1/2024 | Krawiec | A61F 2/4455 |

FOREIGN PATENT DOCUMENTS

| | | | | |
|---|---|---|---|---|
| DE | 19821048 C1 | * | 3/2000 | ........... A61F 2/4607 |
| EP | 3457956 B1 | * | 7/2020 | ............. A61B 17/14 |
| KR | 20080000571 A | * | 1/2008 | ......... A61B 17/7005 |
| KW | 20080000571 A | * | 9/2007 | |
| WO | WO-2019024741 A1 | * | 2/2019 | ......... A61B 17/7283 |
| WO | WO-2023192019 A1 | * | 10/2023 | |

* cited by examiner

PROXIMAL-FEMUR INTRAOSSEOUS RELEASE DEVICE

CROSS-REFERENCE TO RELATED APPLICATIONS

This application claims priority to Chinese Patent Application No. 202311702387.0 with a filing date of Dec. 12, 2023. The content of the aforementioned application, including any intervening amendments thereto, is incorporated herein by reference.

TECHNICAL FIELD

The present invention relates to the field of femoral treatment technologies, and in particular, to a proximal-femur intraosseous release device.

BACKGROUND

In an early stage of femoral head necrosis, blood can still circulate, and a certain treatment effect can be achieved by orally taking medicine, but in a late stage of the femoral head necrosis, the blood is in a non-circulating state, the orally-taken medicine cannot be brought into the femur through the blood, and therefore, the medicine is required to be delivered into the femur by an intraosseous release device to treat the interior of the femur. However, for a patient with femoral head necrosis and a bony crack or a fracture of the proximal femur caused by an external force, not only the medicine is required to be injected into the femur of the patient, but also the femur of the patient is required to be fixed, so as to prevent a second injury to the patient.

SUMMARY

The present invention provides a proximal-femur intraosseous release device, so as to solve the technical problem that an existing intraosseous release device cannot fix the femur of a patient, and therefore, a femoral head necrosis patient with a bony crack or a fracture at the proximal femur is prone to secondary injury.

In order to solve the above technical problem, the present invention provides the following technical solution:
a proximal-femur intraosseous release device includes a release mechanism, wherein a primary fixing mechanism is provided at one end of the release mechanism, the primary fixing mechanism includes a first shell, a top cover is movably mounted at a top of the first shell, a limiting ring is provided at a bottom of the first shell, the limiting ring is connected with an inner side wall of the first shell, and a second shell, a first triangular block and a second triangular block are arranged inside the first shell; an outer side wall of the second shell is provided with a thread groove to be screwed to the inner side wall of the first shell through threads, a bottom of the second shell is rotatably connected with the first triangular block, the first triangular block is slidably connected with the inner side wall of the first shell and can slide along a longitudinal direction of the first shell, a bottom surface of the first triangular block is an inclined surface, the second triangular block is located at a bottom of the first triangular block, a top surface of the second triangular block is an inclined surface, and a through hole matched with the second triangular block is formed in a side wall of the first shell; first limiting blocks are further arranged in the first shell, the first limiting blocks are located on two sides of the second triangular block, first stoppers are arranged on the two sides of the second triangular block respectively, the first stopper is located at an end close to a tip of the second triangular block, a transverse groove matched with the first stopper is formed in the first limiting block, a second limiting block is provided at one end of the transverse groove, the second limiting block is located at an end away from the tip of the second triangular block, and a first spring is connected between the second limiting block and the first stopper.

Optionally, a secondary fixing mechanism is provided on one side of the primary fixing mechanism, the secondary fixing mechanism includes a third shell and a connecting portion, the third shell is detachably connected with the connecting portion, and the connecting portion is fixedly connected with the second triangular block.

Optionally, an internal thread ring is provided inside the third shell, the internal thread ring is fixedly connected with an inner side wall of the third shell, a thread shaft is provided in the internal thread ring, the thread shaft is connected with the internal thread ring through threads, a sealing plate is provided at an end of the thread shaft away from the connecting portion, the sealing plate is located inside the third shell, a first torsion block is provided on the sealing plate, and an annular clamping block is provided at the other end of the thread shaft; a positioning end cover is provided at one end of the third shell, the annular clamping block is located inside the positioning end cover, a plurality of cylindrical blocks are arranged on a periphery of the annular clamping block, an inclined surface is provided at an end of the cylindrical block in contact with the annular clamping block, the annular clamping block is provided with a conical surface matched with the inclined surface of the cylindrical block, a positioning column is provided at an end of the cylindrical block away from the annular clamping block, and a third limiting hole matched with the positioning column is formed in a side wall of the positioning end cover; the positioning column is sleeved with a second spring, one end of the second spring is connected with an end surface of the cylindrical block, the other end of the second spring is connected with an inner side wall of the positioning end cover, the positioning end cover is sleeved with the connecting portion, and a second limiting hole matched with the positioning column is formed in a side wall of the connecting portion.

Optionally, the positioning end cover is provided with a plurality of limiting clamping plates, the limiting clamping plates are arranged on the periphery of the annular clamping block, and the limiting clamping plates and the cylindrical blocks are arranged at intervals.

Optionally, the release mechanism includes a positioning tube, one end of the positioning tube is located inside the primary fixing mechanism and has an end portion with a movably-mounted torsion cover, and a second torsion block is provided on the torsion cover; a rotating shaft is provided in the positioning tube, one end of the rotating shaft is connected with the torsion cover, the other end of the rotating shaft is connected with a gear, racks are connected to two sides of the gear in a meshed mode respectively, the rack is slidably connected with a sliding seat, a medicine liquid bin is provided in the positioning tube, and the sliding seat is mounted in a clamping groove of the medicine liquid bin; a plurality of medicine liquid holes for containing medicine liquid are formed in the medicine liquid bin, a sealing film is provided at a top end of the medicine liquid hole, a bottom plate is provided at a bottom of the medicine liquid bin, and the sealing film corresponding to the medicine liquid hole is provided on the bottom plate; the rotating shaft is sleeved with an annular baffle, a third spring is provided at a bottom of the annular baffle, an annular base is provided at a bottom of the third spring, and sealing columns corresponding to the medicine liquid holes one by one are arranged at a bottom of the annular base; a second stopper is provided on the rack, and when the release mechanism is in an initial state, the second stopper is located at a top of the corresponding medicine liquid hole and a bottom of the corresponding sealing column.

Optionally, a plurality of liquid outlet holes are formed in a side wall of the positioning tube.

Optionally, the primary fixing mechanism further includes a positioning ring, the positioning ring includes an inner ring, a connecting beam and an outer ring, the inner ring is connected with the torsion cover, the connecting beam is configured to connect the inner ring and the outer ring, and a through hole matched with the inner ring, a groove matched with the connecting beam and an annular groove matched with the outer ring are formed in a top of the second shell; an arc-shaped groove is formed in one side of the groove, a first limiting hole is formed in an end portion of the arc-shaped groove, and a clamping block matched with the arc-shaped groove and the first limiting hole is provided on one side of the connecting beam.

Optionally, a bearing ring is provided at a top of the first triangular block, and the bearing ring is sleeved with the second shell.

Optionally, one side of the first triangular block is provided with a first slider, and a first chute matched with the first slider is formed in the inner side wall of the first shell.

Optionally, a second slider is provided on a back surface of the rack, and a second chute matched with the second slider is formed in a side surface of the sliding seat.

The above technical solution of the present invention has the following beneficial effects.

In the above solution, the proximal-femur intraosseous release device can release medicine and fix the femur of the patient, and the second shell is rotated to drive the first triangular block to move downwards, such that the second triangular block is ejected out of the first shell to fix a fracture part of the patient; the second shell is reversely rotated to drive the first triangular block to move upwards, and the second triangular block is restored to the interior of the first shell under the action of an elastic force of the first spring.

Figure 1:
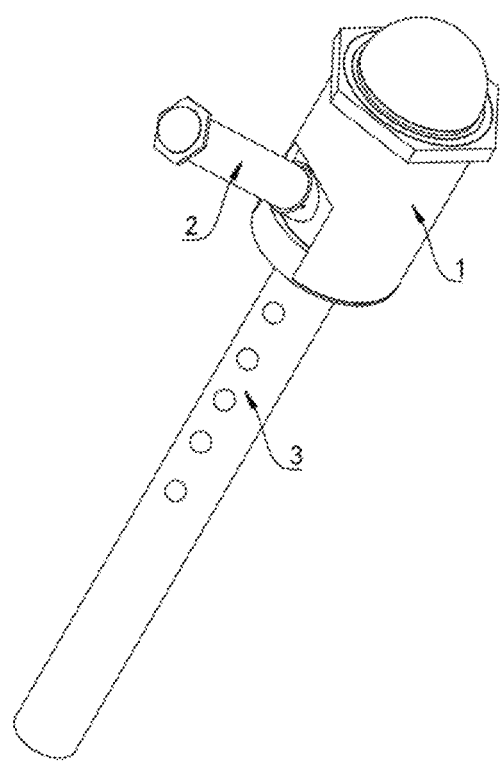
FIG. 1 is a schematic structural diagram of a proximal-femur intraosseous release device according to the present invention.

REFERENCE NUMERALS 1. primary fixing mechanism;
101. first shell; 102. top cover; 103. first chute; 104. limiting ring;
105. first limiting block; 106. second limiting block; 107. second shell;
108. thread groove;
109. annular groove; 110. arc-shaped groove; 111. first limiting hole;
112. positioning ring;
113. clamping block; 114. bearing ring; 115. first triangular block; 116. first slider;
117. second triangular block; 118. first stopper; 119. first spring; 2. secondary fixing mechanism;
201. third shell; 202. connecting portion; 203. second limiting hole; 204. sealing plate;
205. first torsion block; 206. thread shaft; 207. internal thread ring; 208. annular clamping block;
209. limiting clamping plate; 210. cylindrical block; 211. second spring;
212. positioning column;
213. positioning end cover; 214. third limiting hole;
3. release mechanism;
301. torsion cover; 302. rotating shaft; 303. positioning tube; 304. annular baffle;
305. third spring; 306. annular base; 307. sealing column; 308. sliding seat;
309. second chute; 310. rack; 311. second stopper; 312. gear;
314. bottom plate; 315. medicine liquid bin; 316. clamping groove; 317. medicine liquid hole.

DETAILED DESCRIPTION

To make the technical problems, technical solutions and advantages of the present invention more apparent, the following detailed description is given with reference to the accompanying drawings and specific embodiments.

As shown in FIGS. 1 to 11, an embodiment of the present invention provides a proximal-femur intraosseous release device, including a release mechanism 3, wherein a primary fixing mechanism 1 is provided at one end of the release mechanism 3, the primary fixing mechanism 1 includes a first shell 101, a top cover 102 is movably mounted at a top of the first shell 101, a limiting ring 104 is provided at a bottom of the first shell 101, the limiting ring 104 is connected with an inner side wall of the first shell 101, and a second shell 107, a first triangular block 115 and a second triangular block 117 are arranged inside the first shell 101; an outer side wall of the second shell 107 is provided with a thread groove 108 to be screwed to the inner side wall of the first shell 101 through threads, a bottom of the second shell 107 is rotatably connected with the first triangular block 115, the first triangular block 115 is slidably connected with the inner side wall of the first shell 101 and can slide along a longitudinal direction of the first shell 101, a bottom surface of the first triangular block 115 is an inclined surface, the second triangular block 117 is located at a bottom of the first triangular block 115, a top surface of the second triangular block 117 is an inclined surface, and a through hole matched with the second triangular block 117 is formed in a side wall of the first shell 101.

Figure 4:
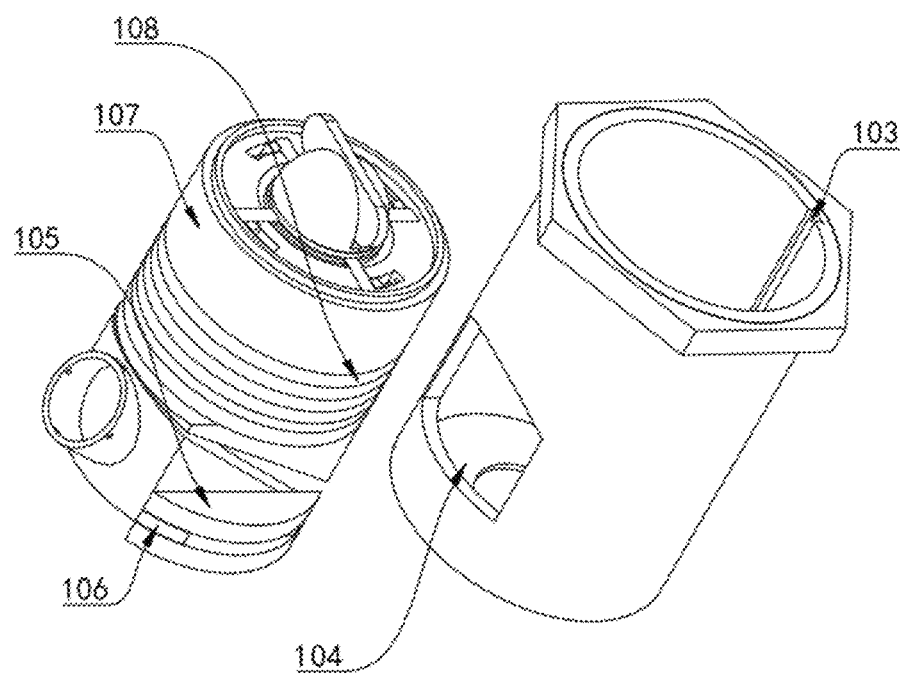
FIG. 4 is a schematic diagram of a first shell and an internal structure of the primary fixing mechanism in the present invention.
Figure 5:
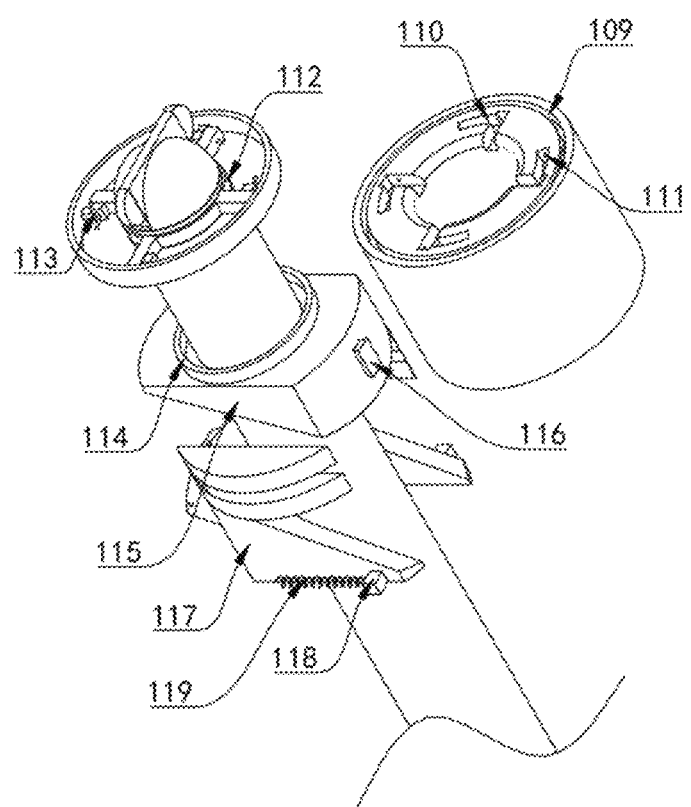
FIG. 5 is a schematic exploded diagram of the internal structure of the primary fixing mechanism in the present invention.

As shown in FIGS. 4 and 5, first limiting blocks 105 are further arranged in the first shell 101, the first limiting blocks 105 are located on two sides of the second triangular block 117, first stoppers 118 are arranged on the two sides of the second triangular block 117 respectively, the first stopper 118 is located at an end close to a tip of the second triangular block 117, a transverse groove matched with the first stopper 118 is formed in the first limiting block 105, a second limiting block 106 is provided at one end of the transverse groove, the second limiting block 106 is located at an end away from the tip of the second triangular block 117, and a first spring 119 is connected between the second limiting block 106 and the first stopper 118.

When the second shell 107 rotates, the first triangular block 115 can be driven to move downwards, such that the second triangular block 117 is ejected out of the first shell 101 under the action of the inclined surface to fix a fracture part of a patient. An outer side surface of the first limiting block 105 is in an arc shape matched with a shape of the inner side wall of the first shell 101, and the first limiting block 105 is fixed inside the first shell 101. When the second triangular block 117 is pressed by the first triangular block 115 to move, the first stopper 118 is simultaneously driven to move in the transverse groove of the first limiting block 105 to compress the first spring 119; when the first triangular block 115 moves upwards, a stretching elastic force of the first spring 119 is transmitted to the first stopper 118 and the second triangular block 117, and the second triangular block 117 is restored to the interior of the first shell 101 under the action of the elastic force of the first spring 119.

Figure 6:
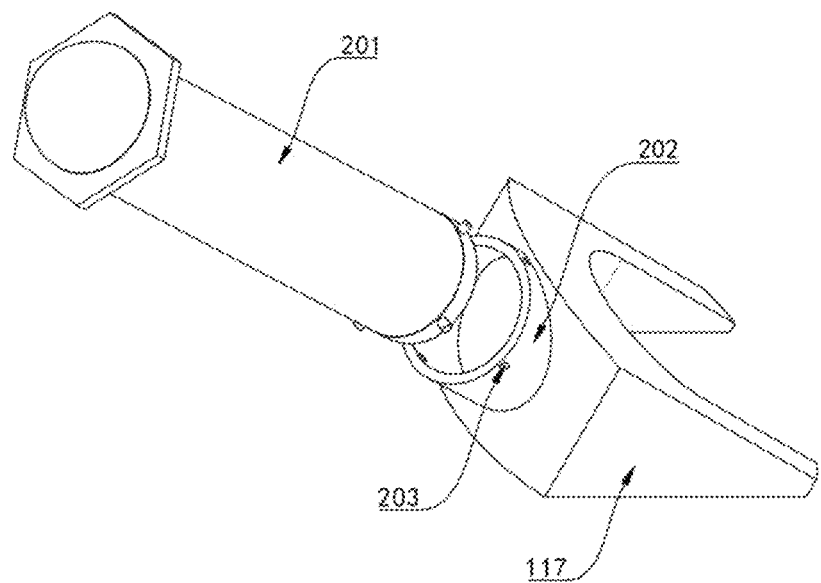
FIG. 6 is a schematic structural diagram of a secondary fixing mechanism in the present invention.

As shown in FIGS. 1 and 6, a secondary fixing mechanism 2 is provided on one side of the primary fixing mechanism 1, the secondary fixing mechanism 2 includes a third shell 201 and a connecting portion 202, the third shell 201 is detachably connected with the connecting portion 202, and the connecting portion 202 is fixedly connected with the second triangular block 117. The secondary fixing mechanism 2 is configured to limit rotation of the primary fixing mechanism 1 around an axis thereof, and the phenomenon that the primary fixing mechanism 1 loosens under the action of an external force after the fracture part of the patient is fixed for a long time can be avoided by providing the secondary fixing mechanism 2.

Figure 7:
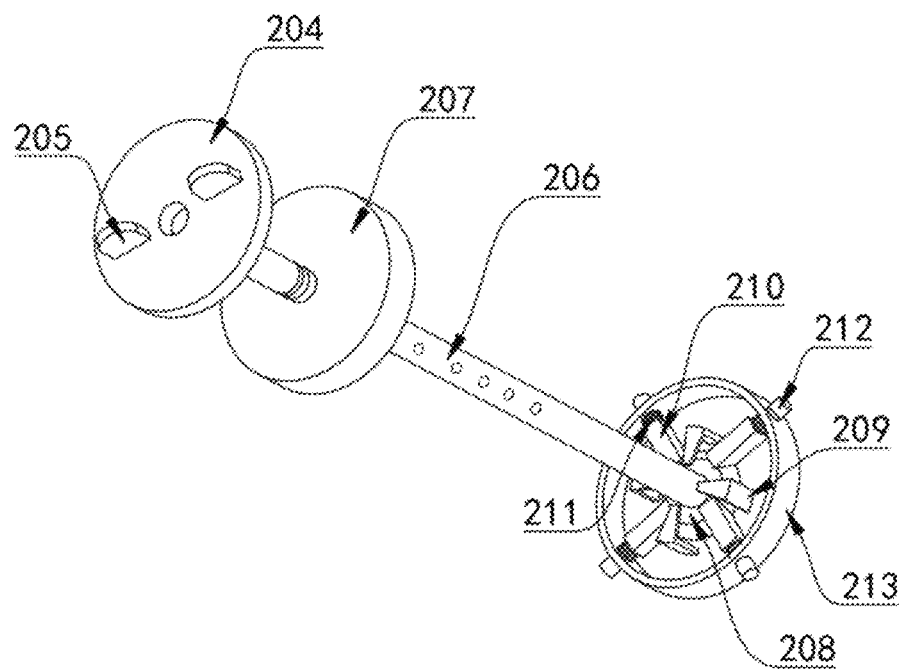
FIG. 7 is a schematic diagram of an internal structure of the secondary fixing mechanism in the present invention.
Figure 8:
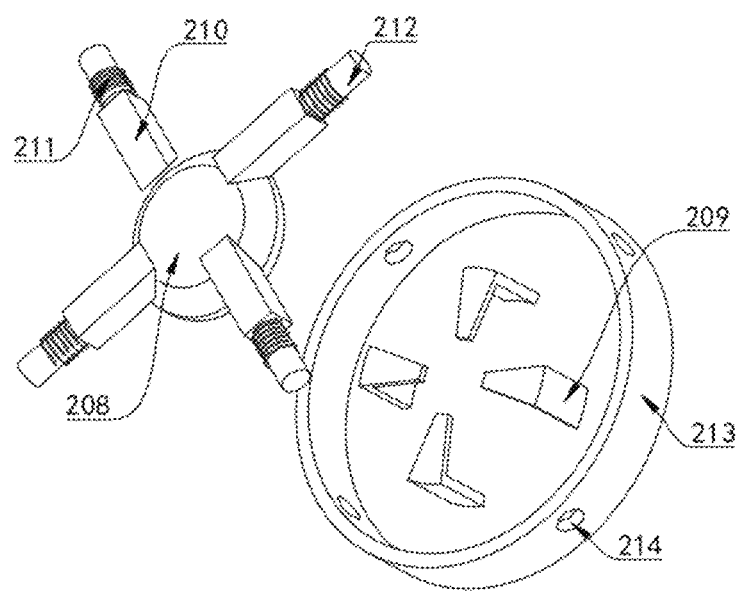
FIG. 8 is a schematic partial exploded diagram of the secondary fixing mechanism in the present invention.

As shown in FIGS. 6 to 8, an internal thread ring 207 is provided inside the third shell 201, the internal thread ring 207 is fixedly connected with an inner side wall of the third shell 201, a thread shaft 206 is provided in the internal thread ring 207, the thread shaft 206 is connected with the internal thread ring 207 through threads, a sealing plate 204 is provided at an end of the thread shaft 206 away from the connecting portion 202, the sealing plate 204 is located inside the third shell 201, a first torsion block 205 is provided on the sealing plate 204, and an annular clamping block 208 is provided at the other end of the thread shaft 206; a positioning end cover 213 is provided at one end of the third shell 201, the annular clamping block 208 is located inside the positioning end cover 213, a plurality of cylindrical blocks 210 are arranged on a periphery of the annular clamping block 208, an inclined surface is provided at an end of the cylindrical block 210 in contact with the annular clamping block 208, the annular clamping block 208 is provided with a conical surface matched with the inclined surface of the cylindrical block 210, a positioning column 212 is provided at an end of the cylindrical block 210 away from the annular clamping block 208, and a third limiting hole 214 matched with the positioning column 212 is formed in a side wall of the positioning end cover 213; the positioning column 212 is sleeved with a second spring 211, one end of the second spring 211 is connected with an end surface of the cylindrical block 210, the other end of the second spring 211 is connected with an inner side wall of the positioning end cover 213, the positioning end cover 213 is sleeved with the connecting portion 202, and a second limiting hole 203 matched with the positioning column 212 is formed in a side wall of the connecting portion 202.

After the second triangular block 117 is ejected out of the first shell 101, the secondary fixing mechanism 2 and the primary fixing mechanism 1 may be fixedly mounted, the third shell 201 is placed inside a hole formed in one side of the femur, and the first torsion block 205 is then rotated to drive the thread shaft 206 to rotate, so as to drive the annular clamping block 208 to move along an axial direction of the thread shaft 206; when the annular clamping block 208 moves upwards, the positioning column 212 is pushed to penetrate through the third limiting hole 214 and the second limiting hole 203, so as to fixedly connect the third shell 201 and the connecting portion 202, and when the annular clamping block 208 moves downwards, the positioning column 212 retracts under the action of the second spring 211.

As shown in FIG. 7, the positioning end cover 213 is provided with a plurality of limiting clamping plates 209, the limiting clamping plates 209 are arranged on the periphery of the annular clamping block 208, and the limiting clamping plates 209 and the cylindrical blocks 210 are arranged at intervals. When moving upwards, the annular clamping block 208 is limited by the limiting clamping plate 209, so as to prevent the annular clamping block 208 from being separated from the cylindrical block 210.

Figure 9:
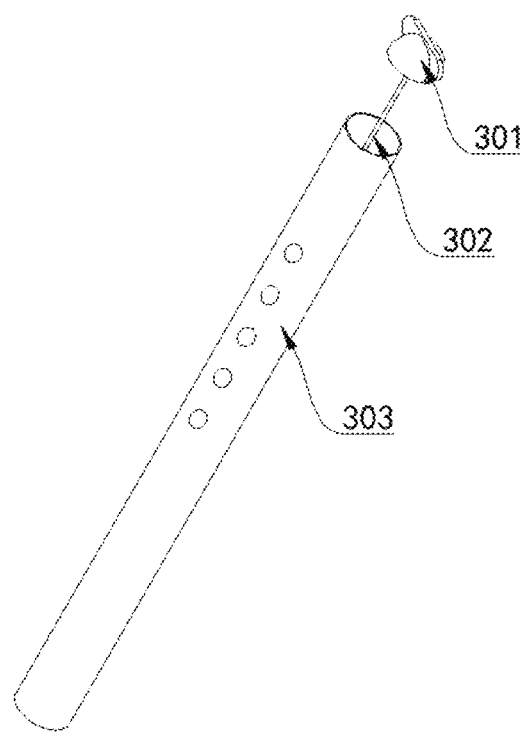
FIG. 9 is a schematic structural diagram of a release mechanism in the present invention.
Figure 10:
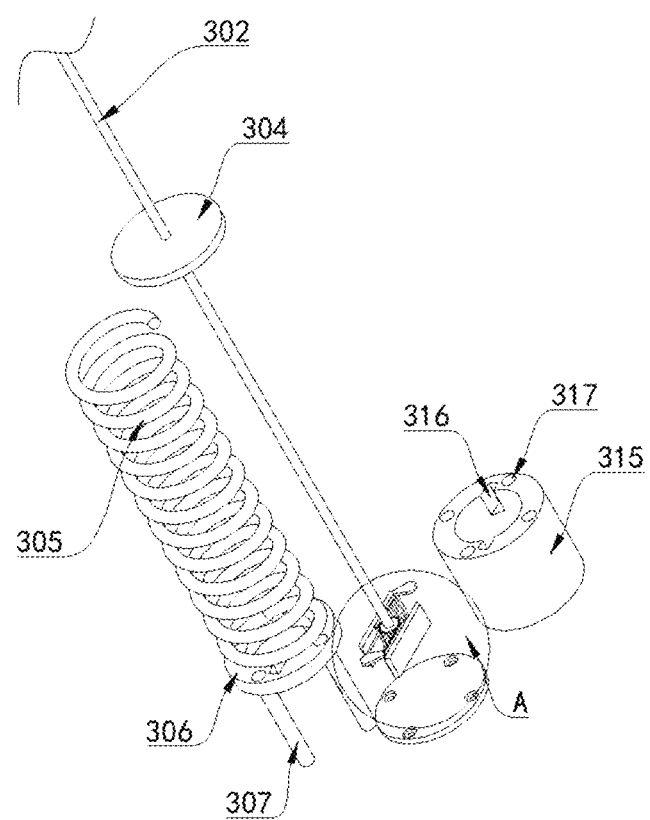
FIG. 10 is a schematic exploded diagram of an internal structure of the release mechanism in the present invention.
Figure 11:
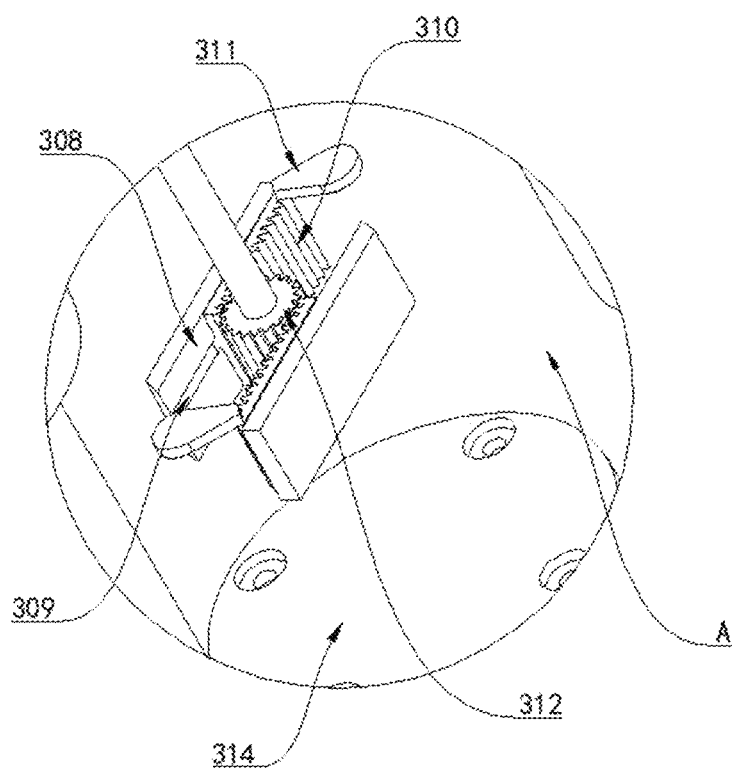
FIG. 11 is a schematic partial enlarged diagram of A in FIG. 10.

As shown in FIGS. 9 to 11, the release mechanism 3 includes a positioning tube 303, one end of the positioning tube 303 is located inside the primary fixing mechanism 1 and has an end portion with a movably-mounted torsion cover 301, and a second torsion block is provided on the torsion cover 301; a rotating shaft 302 is provided in the positioning tube 303, one end of the rotating shaft 302 is connected with the torsion cover 301, the other end of the rotating shaft 302 is connected with a gear 312, racks 310 are connected to two sides of the gear 312 in a meshed mode respectively, the rack 310 is slidably connected with a sliding seat 308, a medicine liquid bin 315 is provided in the positioning tube 303, and the sliding seat 308 is mounted in a clamping groove 316 of the medicine liquid bin 315; a plurality of medicine liquid holes 317 for containing medicine liquid are formed in the medicine liquid bin 315, a sealing film is provided at a top end of the medicine liquid hole 317, a bottom plate 314 is provided at a bottom of the medicine liquid bin 315, and the sealing film corresponding to the medicine liquid hole 317 is provided on the bottom plate 314, such that the medicine liquid hole 317 forms a closed cavity; the rotating shaft 302 is sleeved with an annular baffle 304, a third spring 305 is provided at a bottom of the annular baffle 304, an annular base 306 is provided at a bottom of the third spring 305, and sealing columns 307 corresponding to the medicine liquid holes 317 one by one are arranged at a bottom of the annular base 306; a second stopper 311 is provided on the rack 310, and when the release mechanism 3 is in an initial state, the second stopper 311 is located at a top of the corresponding medicine liquid hole 317 and a bottom of the corresponding sealing column 307.

In use, the second torsion block on the torsion cover 301 is rotated to drive the rotating shaft 302 to rotate, so as to drive the gear 312 to be meshed with the rack 310 for transmission; the rack 310 drives the second stopper 311 to move to be separated from the medicine liquid hole 317 and the sealing column 307, the sealing column 307 pierces the sealing film under the action of the third spring 305 and enters the medicine liquid hole 317, and the medicine liquid in the medicine liquid hole 317 passes through the sealing film on the bottom plate 314 under a pressure and enters the femur of the patient to perform medication on the femur.

Figure 2:
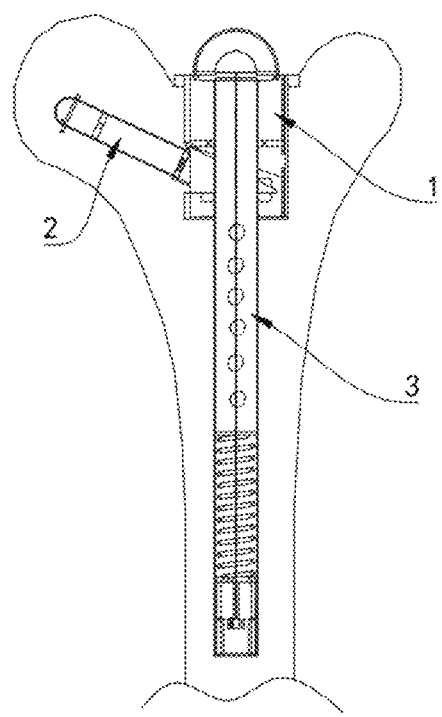
FIG. 2 is a sectional view of the proximal-femur intraosseous release device according to the present invention.
Figure 3:
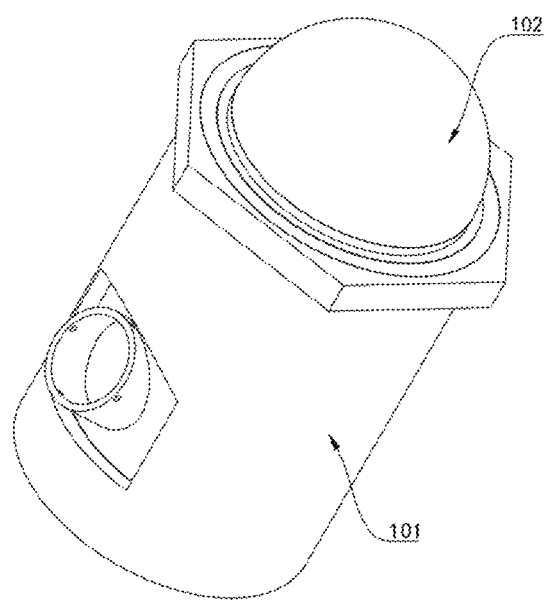
FIG. 3 is a schematic structural diagram of a primary fixing mechanism in the present invention.

As shown in FIGS. 2 and 9, a plurality of liquid outlet holes are formed in a side wall of the positioning tube 303, and when the positioning tube 303 enters the femur, the volatile solid medicine liquid encapsulated inside the positioning tube 303 in advance can permeate into the femur through the liquid outlet holes to treat a lesion.

As shown in FIG. 5, the primary fixing mechanism 1 further includes a positioning ring 112, the positioning ring 112 includes an inner ring, a connecting beam and an outer ring, the positioning tube 303 is sleeved with the inner ring, the connecting beam is configured to connect the inner ring and the outer ring, and a through hole matched with the inner ring, a groove matched with the connecting beam and an annular groove 109 matched with the outer ring are formed in a top of the second shell 107; an arc-shaped groove 110 is formed in one side of the groove, a first limiting hole 111 is formed in an end portion of the arc-shaped groove 110, and a clamping block 113 matched with the arc-shaped groove 110 and the first limiting hole 111 is provided on one side of the connecting beam. The positioning ring 112 is clamped to the arc-shaped groove 110 by rotating the clamping block 113, and the arc-shaped groove 110 can limit the positioning ring 112 to prevent a position deviation in use.

As shown in FIGS. 4 and 5, a bearing ring 114 is provided at a top of the first triangular block 115, and the bearing ring 114 is sleeved with the second shell 107. One side of the first triangular block 115 is provided with a first slider 116, and a first chute 103 matched with the first slider 116 is formed in the inner side wall of the first shell 101. Under the action of the first slider 116 and the first chute 103, the first triangular block 115 can only move up and down along a direction of the first chute 103.

As shown in FIG. 11, a second slider is provided on a back surface of the rack 310, a second chute 309 matched with the second slider is formed in a side surface of the sliding seat 308, and under the action of the second slider and the second chute 309, the rack 310 is fixed on the sliding seat 308 and can only move horizontally along a direction of the second chute 309.

The proximal-femur intraosseous release device according to the invention has the following use process.

Firstly, holes are drilled in an end portion of the femur and a side surface of the end portion of a patient through a drilling apparatus, the primary fixing mechanism 1 is then placed in the hole of the end portion of the femur with the side having the first chute 103 away from the hole of the side surface of the end portion of the femur, and the second shell 107 is rotated to drive the first triangular block 115 to move downwards, so as to drive the second triangular block 117 to move out of the first shell 101 under the limitation of the first limiting block 105.

The third shell 201 is placed in the hole formed in the side surface of the end portion of the femur, and the first torsion block 205 is rotated to drive the sealing plate 204 and the thread shaft 206 to rotate, so as to further drive the annular clamping block 208 to move upwards; the positioning column 212 is ejected out of the positioning end cover 213 by the annular clamping block 208 to be clamped inside the second limiting hole 203, thus completing fixed mounting between the primary fixing mechanism 1 and the secondary fixing mechanism 2.

When disassembly is required, the first torsion block 205 is rotated reversely to drive the thread shaft 206 to rotate, so as to further drive the annular clamping block 208 to move downwards; the cylindrical block 210 and the positioning column 212 are restored under the action of the second spring 211, and the primary fixing mechanism 1 is separated from the secondary fixing mechanism 2.

Finally, the whole release mechanism 3 is placed inside the femur of the patient through the positioning ring 112, the release mechanism 3 is fixedly connected with the positioning ring 112, and the second torsion block on the torsion cover 301 is rotated to drive the rotating shaft 302 to rotate, so as to drive the gear 312 to be meshed with the rack 310 for transmission; the rack 310 drives the second stopper 311 to move towards the gear 312 to be separated from the medicine liquid hole 317 and the sealing column 307, the sealing column 307 pierces the sealing film under the action of the third spring 305 and enters the medicine liquid hole 317, and the medicine liquid in the medicine liquid hole 317 passes through the sealing film on the bottom plate 314 under a pressure and enters the femur of the patient to perform medication on the femur.

In the above solution, the proximal-femur intraosseous release device can release medicine and fix the femur of the patient, and the second shell is rotated to drive the first triangular block to move downwards, such that the second triangular block is ejected out of the first shell to fix a fracture part of the patient; when the primary fixing mechanism and the secondary fixing mechanism are required to be connected, the positioning column can extend out of the positioning end cover by rotating the first torsion block and is clamped in the second limiting hole, so as to complete the fixed mounting between the primary fixing mechanism and the secondary fixing mechanism; by rotating the second torsion block, the medicine liquid stored in the medicine liquid hole in advance can be extruded and released into the femur of the patient to perform medication on the interior of the femur of the patient.

The foregoing is a preferred implementation of the present invention, and it should be noted that, for those skilled in the art, various improvements and modifications can be made without departing from the principle of the present invention, and these improvements and modifications should also be considered as the protection scope of the present invention.

What is claimed is:

1. A proximal-femur intraosseous release device, comprising a release mechanism, wherein a primary fixing mechanism is provided at one end of the release mechanism, the primary fixing mechanism comprises a first shell, a top cover is movably mounted at a top of the first shell, a limiting ring is provided at a bottom of the first shell, the limiting ring is connected with an inner side wall of the first shell, and a second shell, a first triangular block and a second triangular block are arranged inside the first shell;

an outer side wall of the second shell is provided with a thread groove to be screwed to the inner side wall of the first shell through threads, a bottom of the second shell is rotatably connected with the first triangular block, the first triangular block is slidably connected with the inner side wall of the first shell and is capable of sliding along a longitudinal direction of the first shell, a bottom surface of the first triangular block is a first inclined surface, the second triangular block is located at a bottom of the first triangular block, a top surface of the second triangular block is a second inclined surface and a through hole matched with the second triangular block is formed in a side wall of the first shell;

first limiting blocks are further arranged in the first shell, the first limiting blocks are located on two sides of the second triangular block, first stoppers are arranged on the two sides of the second triangular block respectively, the first stopper is located at an end close to a tip of the second triangular block, a transverse groove matched with the first stopper is formed in the first limiting block, a second limiting block is provided at one end of the transverse groove, the second limiting block is located at an end away from the tip of the second triangular block, and a first spring is connected between the second limiting block and the first stopper.

2. The proximal-femur intraosseous release device according to claim 1, wherein a secondary fixing mechanism is provided on one side of the primary fixing mechanism, the secondary fixing mechanism comprises a third shell and a connecting portion, the third shell is detachably connected with the connecting portion, and the connecting portion is fixedly connected with the second triangular block.

3. The proximal-femur intraosseous release device according to claim 2, wherein an internal thread ring is provided inside the third shell, the internal thread ring is fixedly connected with an inner side wall of the third shell, a thread shaft is provided in the internal thread ring, the thread shaft is connected with the internal thread ring through threads, a sealing plate is provided at an end of the thread shaft away from the connecting portion, the sealing plate is located inside the third shell, a first torsion block is provided on the sealing plate, and an annular clamping block is provided at the other end of the thread shaft;

a positioning end cover is provided at one end of the third shell, the annular clamping block is located inside the positioning end cover, a plurality of cylindrical blocks are arranged on a periphery of the annular clamping block, a third inclined surface is provided at an end of the cylindrical block in contact with the annular clamping block, the annular clamping block is provided with a conical surface matched with the third inclined surface of the cylindrical block, a positioning column is provided at an end of the cylindrical block away from the annular clamping block, and a third limiting hole matched with the positioning column is formed in a side wall of the positioning end cover;

the positioning column is sleeved with a second spring, one end of the second spring is connected with an end surface of the cylindrical block, the other end of the second spring is connected with an inner side wall of the positioning end cover, the positioning end cover is sleeved with the connecting portion, and a second limiting hole matched with the positioning column is formed in a side wall of the connecting portion.

4. The proximal-femur intraosseous release device according to claim 3, wherein the positioning end cover is provided with a plurality of limiting clamping plates, the limiting clamping plates are arranged on the periphery of the annular clamping block, and the limiting clamping plates and the cylindrical blocks are arranged at intervals.

5. The proximal-femur intraosseous release device according to claim 1, wherein the release mechanism comprises a positioning tube, one end of the positioning tube is located inside the primary fixing mechanism and has an end portion with a movably-mounted torsion cover, and a second torsion block is provided on the torsion cover;

a rotating shaft is provided in the positioning tube, one end of the rotating shaft is connected with the torsion cover, the other end of the rotating shaft is connected with a gear, racks are connected to two sides of the gear in a meshed mode respectively, the rack is slidably connected with a sliding seat, a medicine liquid bin is provided in the positioning tube, and the sliding seat is mounted in a clamping groove of the medicine liquid bin;

a plurality of medicine liquid holes for containing medicine liquid are formed in the medicine liquid bin, a sealing film is provided at a top end of the medicine liquid hole, a bottom plate is provided at a bottom of the medicine liquid bin, and the sealing film corresponding to the medicine liquid hole is provided on the bottom plate;

the rotating shaft is sleeved with an annular baffle, a third spring is provided at a bottom of the annular baffle, an annular base is provided at a bottom of the third spring, and sealing columns corresponding to the medicine liquid holes one by one are arranged at a bottom of the annular base;

a second stopper is provided on the rack, and when the release mechanism is in an initial state, the second stopper is located at a top of the corresponding medicine liquid hole and a bottom of the corresponding sealing column.

6. The proximal-femur intraosseous release device according to claim 5, wherein a plurality of liquid outlet holes are formed in a side wall of the positioning tube.

7. The proximal-femur intraosseous release device according to claim 5, wherein the primary fixing mechanism further comprises a positioning ring, the positioning ring comprises an inner ring, a connecting beam and an outer ring, the inner ring is connected with the torsion cover, the connecting beam is configured to connect the inner ring and the outer ring, and a through hole matched with the inner ring, a groove matched with the connecting beam and an annular groove matched with the outer ring are formed in a top of the second shell;

an arc-shaped groove is formed in one side of the groove, a first limiting hole is formed in an end portion of the arc-shaped groove, and a clamping block matched with the arc-shaped groove and the first limiting hole is provided on one side of the connecting beam.

8. The proximal-femur intraosseous release device according to claim 1, wherein a bearing ring is provided at a top of the first triangular block, and the bearing ring is sleeved with the second shell.

9. The proximal-femur intraosseous release device according to claim 1, wherein one side of the first triangular block is provided with a first slider, and a first chute matched with the first slider is formed in the inner side wall of the first shell.

10. The proximal-femur intraosseous release device according to claim 5, wherein a second slider is provided on a back surface of the rack, and a second chute matched with the second slider is formed in a side surface of the sliding seat.

* * * * *